United States Patent [19]

Hauffe

[11] Patent Number: 5,165,795
[45] Date of Patent: Nov. 24, 1992

[54] METHOD OF DETERMINING THE WEIGHT OF CONVERSION LAYERS PER UNIT OF AREA

[75] Inventor: Dieter Hauffe, Frankfurt am Main, Fed. Rep. of Germany

[73] Assignee: Metallgesellschaft Aktiengesellschaft, Frankfurt am Main, Fed. Rep. of Germany

[21] Appl. No.: 727,427

[22] Filed: Jul. 9, 1991

[30] Foreign Application Priority Data

Jul. 9, 1990 [DE] Fed. Rep. of Germany ....... 4021792

[51] Int. Cl.⁵ .......................................... G01N 25/00
[52] U.S. Cl. ........................................ 314/45; 374/14
[58] Field of Search .................................. 374/45, 14

[56] References Cited

U.S. PATENT DOCUMENTS

| 921,083 | 5/1909 | Chaney | 374/45 |
|---|---|---|---|
| 1,495,314 | 5/1924 | Walker | 374/45 |
| 3,282,082 | 11/1966 | Fagioli et al. | 374/45 |
| 3,354,317 | 11/1967 | Gamble et al. | 374/45 |
| 3,413,474 | 11/1968 | Freeh et al. | 374/123 |
| 3,453,866 | 7/1969 | Simon | 374/45 |
| 4,281,533 | 8/1981 | Eesley et al. | 374/43 |
| 4,594,510 | 6/1986 | Brown et al. | 374/43 |
| 4,705,409 | 11/1987 | Trerice | 374/45 |
| 4,831,258 | 5/1989 | Paulk et al. | 374/121 |

FOREIGN PATENT DOCUMENTS

| 0195168 | 9/1986 | European Pat. Off. |  |
|---|---|---|---|
| 0122524 | 6/1986 | Japan | 374/45 |
| 0043550 | 2/1987 | Japan | 374/45 |

Primary Examiner—Allan N. Shoap
Assistant Examiner—Diego F. F. Gutierrez
Attorney, Agent, or Firm—Herbert Dubno

[57] ABSTRACT

A method of determining the weight per unit of area of conversion layers, particularly of phosphate layers, on metals, in which the heat radiated from the dry surface which is covered with the conversion layer and is at the temperature T and the heat radiated from a reference surface or a reference cavity which is at the temperature $T+t$ are periodically measured at a temperature between 15° and 50° C. by a wavelength-insensitive electic infrared detector. t is preferably selected in the range from $+15°$ to $+3°$ C. from $-15°$ to $-3°$ C. above or below T. The weight of the conversion layer per unit of area is determined from the amplitude of the resulting electric alternating signal. The radiant heat is suitable measured by an infrared detector having a sensor which consists of a pyroelectric sheet of polyvinylidene fluoride.

9 Claims, 2 Drawing Sheets

METHOD OF DETERMINING THE WEIGHT OF CONVERSION LAYERS PER UNIT OF AREA

FIELD OF THE INVENTION

My present invention relates to a method of determining the weight per unit of area (specific weight or basis weight) of conversion layers, particularly phosphate layers, on metals.

BACKGROUND OF THE INVENTION

Conversion layers on metals are extensively used in industry, inter alia, to increase the resistance to corrosion, as a pretreatment for subsequent painting, to facilitate non-cutting cold working and running-in operations (reduction of sliding friction) and for electrical insulation. Layers based on the phosphates of Zn, Mn, Fe, Ca, Ni, Mg, and other cations have achieved special significance, and the layer may contain one or more of these cations.

An important parameter of the conversion layers is their weight per unit of area (also referred to herein as wt/A, specific weight, basis weight) because different ranges of that parameter will give optimum results in different fields of application and that parameter must be kept within a more or less narrow range for a trouble-free series production.

The weight per unit of area, which is also a measure of thickness for a given layer composition, is usually stated in grams of the layer material per square meter of the surface area ($g/m^2$) and can be measured by the stripping method (dissolution method) involving differential weighing or by a determination of one or more components of the layer by chemical analysis, X-ray fluorescence, infrared absorption, GDOS (glow discharge optical spectroscopy) and/or other methods.

The stripping method is a destructive test and for this reason is less suitable for production control. X-ray fluorescence, infrared absorption and glow discharge optical spectroscopy require expensive analyzing apparatus. Probing devices that make use of the weakening of the adhesive force of a permanent magnet, or the influencing of the magnetic flux or the weakening of the induction effected by a high-frequency alternating current are less suitable, as a rule, for determining basis weight of conversion layers because the sensing heads may locally damage the layer and because the accuracy of the measurement is low in the range of the thicknesses of the conversion layers used.

OBJECTS OF THE INVENTION

It is an object of the invention to provide an improved method for the determination of the weight per unit area (basis weight) layers, particularly phosphate layers, on metals which is superior to the conventional methods as regards speed, nondestructiveness and the use of simple technical means.

Another object of the invention is to provide an improved apparatus for the determination of basis weight of phosphate conversion coatings on a substrate metal.

SUMMARY OF THE INVENTION

These objects are attained in accordance with the invention by periodically measuring the heat radiated from a dry surface which is covered with the conversion layer and is at the temperature T and the heat radiated from a reference surface or a reference cavity which is at the temperature T+t at a temperature between 15° and 50° C. by means of a wavelength-insensitive electric infrared detector and the weight of the conversion layer per unit of area is determined from the amplitude of the resulting electric alternating signal.

For the purposes of the invention a conversion layer is an inorganic or mixed inorganic-organic layer, which has been formed on a metal by a chemical reaction of a predominantly aqueous solution with the metal surface. Typical examples are layers of chromates, phosphates, oxides, oxalates, complex fluorides, etc.

The layers may be provided on metals of various kinds, such as iron, steel, stainless steel, zinc, zinc alloys, aluminum, aluminum alloys, magnesium, magnesium alloys, titanium, titanium alloys, zirconium and its alloys. But metals having the highest technological significance are steels, low-alloy steel, galvanized steel, zinc alloy-plates steel, aluminized steel, aluminum alloy-plated steel as well as aluminum and its alloys.

Wavelength-insensitive electric infrared detectors are detectors which convert incident infrared radiation to electric signals and are at least largely independent of the radiation spectrum of the surface to be measured and operate in such a manner that at least in a certain energy range the amplitude of the outputed signal is proportional to the intensity of the incident infrared radiation. That property affords, inter alia, the advantage that surfaces provided with conversion layers having different emission spectra can be measured after a suitable calibration.

For the measurement, the infrared detector is periodically directed to the surface (i.e. is trained thereon) which is covered with a conversion layer and to a reference surface or a reference cavity, the temperatures of which differ by a temperature t.

The surfaces must be dry because thin films of water would falsify the measured values by their inherent radiation.

The periodic change is preferably effected by mechanical measures, e.g., by means of a pivoted mirror, a rotating perforated disk or a sliding shutter, in such a manner than an alternating signal with a frequency of about 10 to 0.5 Hertz is obtained. The amplitude of the alternating electric signal, optionally after it has suitably been amplified and smoothened, is calibrated with respect to the weight of the conversion layer per unit of area.

It will be understood that the calibration can be made with respect to other parameters which are proportional to the weight per unit of area, such as the content of certain components in the layer or the thickness of the layer.

The calibration of the measuring means used to carry out the method in accordance with the invention is preferably performed in such a manner that the measured-value signals representing the surface states "bare metal", "metal with conversion layers" for various weights per unit of area, which have been determined, e.g., with the dissolution method, and "black surfaces for infrared" are recorded.

Such a calibration e.g. for zinc phosphate layers on steel, will furnish a curve, which can be used to associate the measured values obtained for individual sample sheets with the actual weight per unit of area or basis weight of the conversion layer.

By means of the method in accordance with the invention, reliable information can be furnished in the range of weights of about 1 to 8 $g/m^2$. The state "black surface for infrared" can be realized, e.g. by a layer of a white-pigmented synthetic resin dispersion paint in a thickness of 30 to 100 μm. The calibration for the surface state "bare metal" may optionally be omitted.

The temperature difference t between the object to be measured and the reference is usually selected in the range from +15° to +3° C. or from −15° to −3° C. with respect to T. It has been found that the temperature T of the surface which is covered with the conversion layer and is to be measured is suitably held at the ambient temperature and the reference is suitably heated.

In a preferred embodiment of the invention the radiant heat is measured with an infrared detector comprising a sensor which consists of a pyroelectric sheet of polyvinylidene fluoride.

BRIEF DESCRIPTION OF THE DRAWING

The above and other objects, features and advantages of my invention will become more readily apparent from the following description, reference being made to the accompanying highly diagrammatic drawing in which.

SPECIFIC DESCRIPTION

Figure 1:
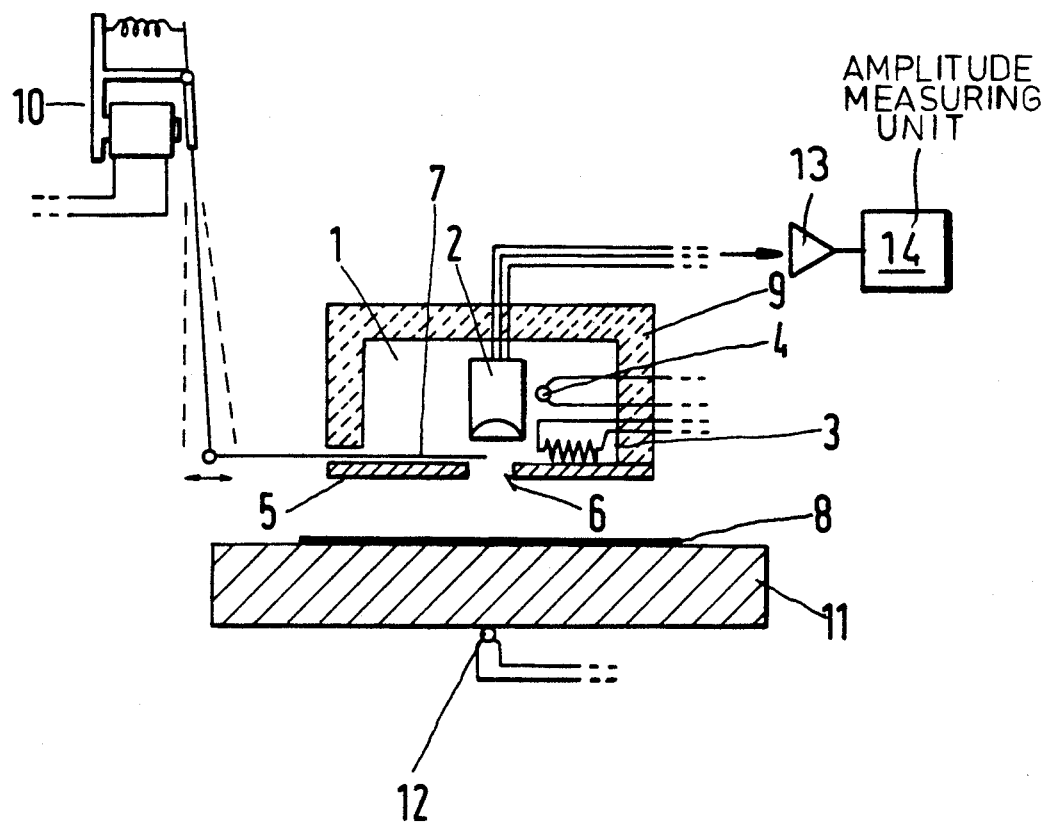
FIG. 1 is a schematic view showing a measuring apparatus.

The measuring apparatus shown by way of example in FIG. 1 comprises a measuring chamber 1, which contains the commercially available infrared detector PID 11, designated 2. The sensor of that detector consists of a pyroelectric sheet of polyvinylidene fluoride. The means of the resistance heater 3 and the temperature sensors 4 the interior of the measuring chamber 1 is kept at a temperature which exceeds the ambient temperature e.g. by +3° C. The measuring chamber is closed at the bottom by a Cu plate 5, which has a window 6 which, by means of the shutter 7, is periodically opened, e.g., for periods of 0.5 second and closed for a period of 0.5 second, for instance. The sample sheet 8 lies on a support 11 under the measuring chamber 1. The support and the sample sheet are at room temperature. The exact temperature is determined by the temperature sensor 12. The distance from the support 11 to the Cu plate 5 is about 15 mm. The heat insulation of the measuring chamber 1 is designated 9 and a solenoid-controlled timer is designated 10 and has its armature 10a connected by the rod 10b to the plate 7 to effect the periodic displacement thereof.

During the change from the "closed" state to the "open" state the infrared detector 2 in operation generates a voltage pulse having an amplitude which depends on the velocity of the opening movement and on the difference between the radiant heats from the surface 8 of the sample sheet and from the interior of the measuring chamber 1. An opposite voltage pulse will result from the closing of the window.

The measured-value signals are amplified at 13 to provide an alternating voltage with a frequency of 1 Hertz. The alternating voltage measured (at an amplitude measuring unit 14) for a bare sample sheet 8 is defined as "0%" and the alternating voltage measured for a sample sheet 8 having a surface which is black for infrared is defined as "100%". Test sheets provided with zinc phosphate layers having various weights per unit of area will give measured values "X %" between zero and 100%. The absorbance (extinction) E was calculated from each measured value X for sample sheets provided with phosphate layers having various weights per unit of area in accordance with the equation $$E = -\log(1 - X/100).$$

Figure 2:
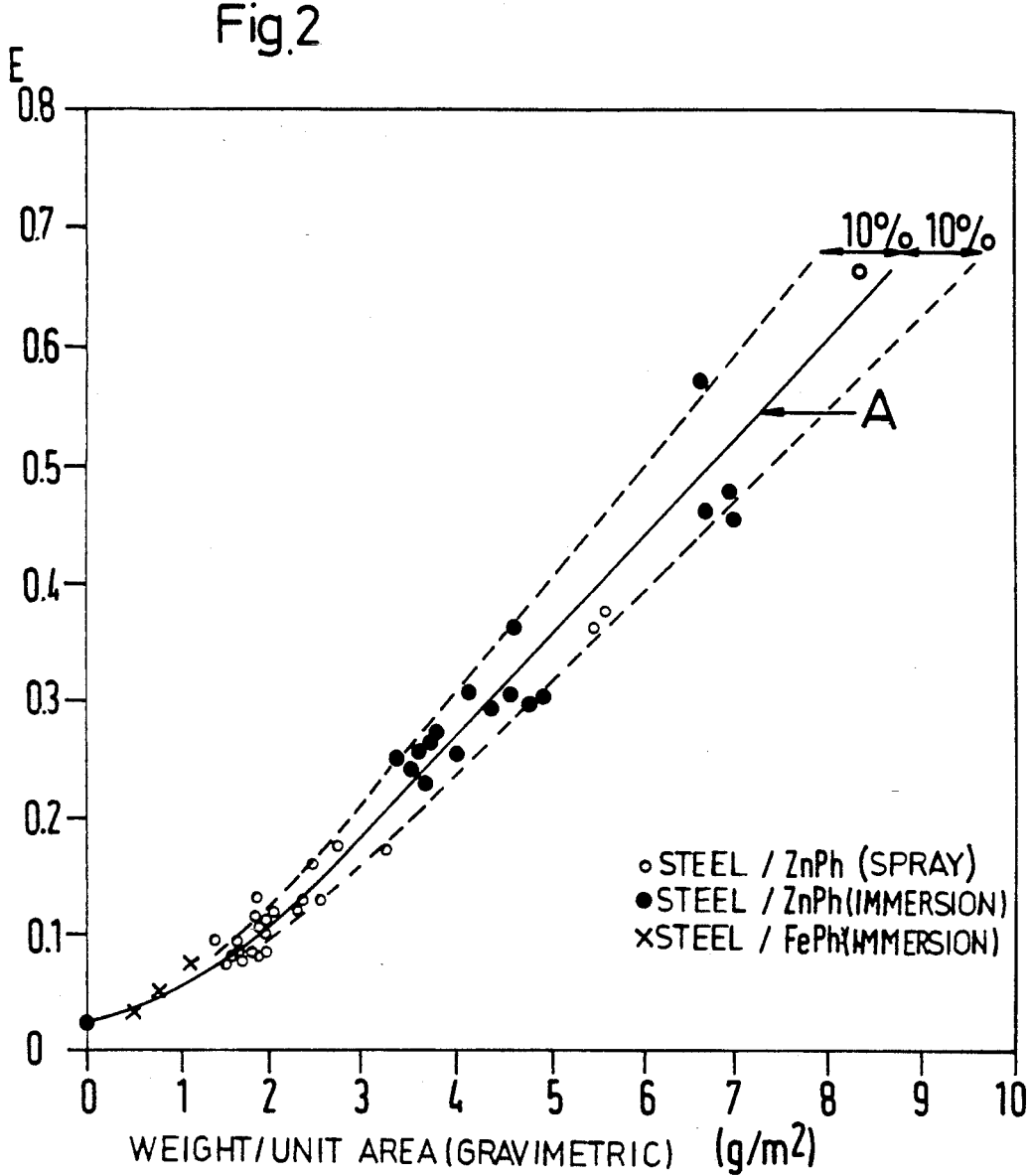
FIG. 2 is a graph which has been established by calibration and in which the absorbance (E) is plotted against the weight per unit of area determined by gravimetry.
Figure 3:
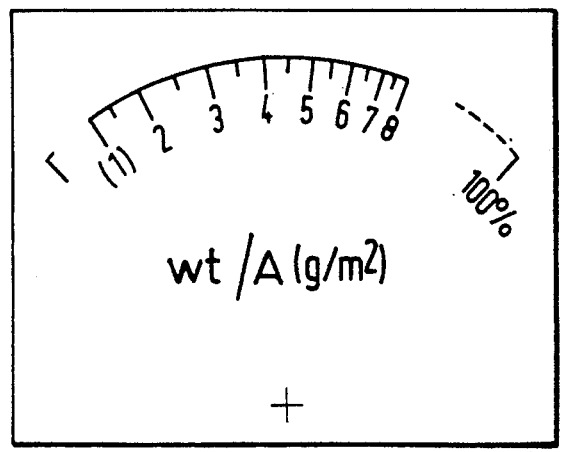
FIG. 3 represents the scale of an indicating device calibrated in weight per unit of area units.

In FIG. 2 the absorbance (extinction) E of the various phosphate layers (spray coated or applied by dip coating, i.e. immersion) are plotted against the weights per unit of area wt/A (g/m$^2$) which had been gravimetrically determined by the stripping method. With the aid of the compensating curve A it is possible to draw a scale by which the measured a.c. signal is directly converted to the desired weight of the phosphate layer per unit of area. Such a scale is shown in FIG. 3.

The method in accordance with the invention can be used for a fast, reliable and nondestructive determination of the weight of conversion layers on metals per unit of area and of parameters which are proportional thereto and has proved to be excellent, e.g. in the production control of phosphate layers on automobile bodies, housing of household appliances, sheet metal parts and strip.

I claim:

1. A method of determining weight per unit of area of a conversion layer on a metal substrate, said method comprising the steps of:
   (a) periodically measuring heat alternately radiated from a dry surface of the substrate which is covered with the conversion layer and is at a temperature T and radiated from a reference surface or a reference cavity which is at a temperature T+t at a temperature between 15° and 50° C. by a common wavelength insensitive electric infrared detector to produce an electric alternating signal of a frequency corresponding to alternation of measurement of radiation at said temperatures T and T+t; and
   (b) measuring an amplitude of said signal to establish the weight of the conversion layer per unit of area based upon a calibration of amplitudes of said signal with weights of the conversion layer per unit of area.

2. The method defined in claim 1 wherein the temperature t is selected in the range from +15° to +3° C. or from −15° to −3° C. with respect to T.

3. The method defined in claim 1, wherein the radiant heat is measured with an infrared detector comprising a sensor which consists of a pyroelectric sheet of polyvinylidene fluoride.

4. The method defined in claim 1 wherein the surfaces of bare metal and of metal provided with conversion layers having various weights per unit of area, and a surface which is black for infrared radiation, are used for the calibration.

5. The method defined in claim 4 wherein the temperature t is selected in the range from +15° to +3° C. or from −15° to −3° C. with respect to T.

6. The method defined in claim 5, wherein the radiant heat is measured with an infrared detector comprising a sensor which consists of a pyroelectric sheet of polyvinylidene fluoride.

7. An apparatus for determining basis weight of a conversion layer on a metal substrate, said apparatus comprising;

means for maintaining said substrate at a temperature T in a range of 15° C. to 50° C. and a reference at a temperature T+t where t=±3° C. to 15° C.;

a wavelength-insensitive electric infrared detector positioned to be directed toward said layer of said substrate and toward said reference;

means for periodically directing said detector toward said layer and toward said reference to generate an electric alternating signal at said detector with a frequency dependent upon the periodic direction of said detector toward said layer and said reference and an amplitude calibrated with basis weight of the conversion layer; and means connected with said detector for determining said basis weight from an amplitude of said signal.

8. The apparatus defined in claim 7 wherein said detector is trained on said layer of said substrate through a window in an insulated cavity receiving said detector, said means for periodically training said detector on said layer and on said reference to generate said electric alternating signal at said detector including a shutter shiftable across said window, and means for periodically shifting said shutter.

9. The apparatus defined in claim 7 wherein said detector has a sensor which consists of a pyroelectric sheet of polyvinylidene fluoride.